(12) United States Patent
Herrema

(10) Patent No.: US 6,982,161 B1
(45) Date of Patent: Jan. 3, 2006

(54) PROCESS FOR THE UTILIZATION OF RUMINANT ANIMAL METHANE EMISSIONS

(76) Inventor: Markus Donald Herrema, 3 Hancock St., Laguna Niguel, CA (US) 92677

( * ) Notice: Subject to any disclaimer, the term of this patent is extended or adjusted under 35 U.S.C. 154(b) by 118 days.

(21) Appl. No.: 10/687,272

(22) Filed: Oct. 15, 2003

(51) Int. Cl.
   *C12N 1/30* (2006.01)
   *A61K 35/42* (2006.01)

(52) U.S. Cl. ............... 435/250; 424/557; 435/252.1; 435/289.1

(58) Field of Classification Search ............... 435/250, 435/252.1, 289.1; 424/543, 557
See application file for complete search history.

(56) References Cited

U.S. PATENT DOCUMENTS

| 4,375,515 A | 3/1983 | Patel et al. |
| 4,524,569 A | 6/1985 | Hanna |
| 5,344,766 A | 9/1994 | Ramachandran et al. |
| H1430 H | 4/1995 | Apel et al. |
| 6,051,411 A | 4/2000 | Turtakovsky et al. |

OTHER PUBLICATIONS

Polakovic, "Getting the Cows to Cool It," Los Angeles Times, Jun. 7, 2003, pp. A1-A17, Los Angeles, CA U.S.A.
Bartle, "Exploiting a Gascating Bacteria," University of Bergen Magazine, 2002, at http://www.uib.no/elin/elpub/uibmag/en02/bacteria.html.
D'Aquino, "Methane to Protein," at http://www.aptagen.com/corporate/AptagenDocuments/Articles/che.html.

*Primary Examiner*—Robert A. Wax
*Assistant Examiner*—Rosanne Kosson

(57) ABSTRACT

A process for the utilization of the methane contained within ruminant animal exhalation, specifically to a process that utilizes the methane contained within ruminant animal exhalation as a source of carbon and/or energy for the production of methane-utilizing microorganisms in a microorganism growth-and-harvest apparatus.

14 Claims, 3 Drawing Sheets

PROCESS FOR THE UTILIZATION OF RUMINANT ANIMAL METHANE EMISSIONS

CROSS-REFERENCE TO RELATED APPLICATION

Not Applicable

FEDERALLY SPONSORED RESEARCH

Not Applicable

SEQUENCE LISTING OR PROGRAM

Not Applicable

BACKGROUND OF THE INVENTION

1. Field of Invention

This invention relates to a process for the utilization of ruminant animal methane emissions, specifically to a process that utilizes the methane contained within ruminant animal exhalation as a source of energy.

2. Prior Art

Methane emissions from ruminant animals account for about twenty percent of total global methane emissions, and atmospheric methane accounts for about twenty percent of planetary warming. In addition to the environmentally destructive effects of ruminant animal methane emissions, such emissions represent wasted energy, as up to thirteen percent of the food ruminant animals eat is lost as methane. Accordingly, there have been significant efforts in the past to reduce ruminant animal methane emissions.

Ruminant animal methane emissions originate in the four-stomach digestive tract common to all ruminant animals, which includes the rumen, a large forestomach connected to the four-stomach digestive tract. The rumen contains a host of digestive enzymes, fungi, bacterium, and protozoa, and the bulk of digestion, as well as methane production, takes place here. Not surprisingly, all prior efforts to reduce methane emissions in ruminant animals, which include dairy cows, cattle, sheep, goats, water buffalo, and camels, have focused on modifications associated with the rumen or digestive tract.

Past modification efforts have included: vaccines designed to limit methanogenic, or methane-producing, microorganisms in the rumen or digestive tract; feed reformulations designed to alter the chemical or microbial environment of the rumen or digestive tract to limit methane production; feed reformulations designed to decrease the amount of methane-producing foods entering the rumen or digestive tract; and selective breeding aimed at encouraging the reproductive success of ruminant animals which produce relatively low amounts of methane, presumably as a result of factors associated with the rumen or digestive tract.

While most of these prior efforts and inventions have had some success in reducing ruminant animal methane emissions, none has been shown to completely, or even significantly, eliminate ruminant animal methane production. Since limited success in reducing methane emissions concurrently limits the economic benefits of using methane-reducing vaccines, feed formulations, or selective breeding, ruminant animal owners have generally been averse or reluctant to employ these methods. Thus, as the ruminant animal population continues to grow in accord with ever-increasing worldwide demand and methane reduction efforts fail to reduce emissions in any significant way, ruminant animal methane emissions remain a major source of both environmental degradation and unutilized energy.

Prior to the applicant's discovery, no methods were known to reduce ruminant animal methane emissions by utilizing such methane as a source of energy in energy consumption systems maintained outside of the digestive tracts of ruminant animals. In the past, all methane reduction processes have focused on limiting ruminant animal methane production rather than reducing emissions through a system of methane utilization. Thus, it is an essential feature of the present invention that ruminant animal methane emissions are significantly reduced through the direct utilization of ruminant animal methane as a source of energy.

Methane-utilizing, or methanotrophic, microorganisms are well-known in the microbiology art for their capacity to grow using methane as a carbon and/or energy source. Methanotrophic microorganisms, specifically bacteria, have even been employed to reduce ruminant animal methane emissions by being placed directly in the rumen or digestive tract of ruminant animals and subsequently limiting production at its source. They have never, though, been employed in a microbiological growth-and-harvest system which concurrently reduces ruminant animal atmospheric methane emissions and provides a means for harvesting the product of microorganism growth (i.e. microorganism biomass).

In short, the connection between ruminant animal methane emissions and methanotrophic growth-and-harvest systems has never been made. At least three major factors have likely contributed to inhibiting such a connection. First, it is not a well-known fact that around ninety-five percent of ruminant animal methane emissions exit the digestive tracts of ruminant animals as exhalation, rather than as flatulence. (The specific physiological pathway of ruminant animal methane emissions is a relatively new discovery.) Most continue to regard such emissions as components of low-volume, diffuse flatulence. Second, it is not a well-known fact that certain ruminant animals produce enough methane to make methanotrophic microorganism growth and harvest systems economically feasible. Consequently, all past ruminant animal methane reduction efforts have focused on decreasing methane production, rather than instituting methane utilization systems. Third, ruminant animal methane capture and conveyance systems have never been employed, largely for the reasons listed above. For these, and probably more, reasons, the connection between ruminant animal exhalation methane emissions and methanotrophic microorganism growth and harvest systems has never occurred.

No previous methods were known to reduce ruminant animal methane emissions by using such methane as a source of energy. Consequently, ruminant animal atmospheric methane emissions remain a significant source of environmental degradation and wasted energy.

The present invention relates to a process for the utilization of ruminant animal exhalation methane as a novel source of energy.

OBJECTS AND ADVANTAGES

Besides the objects and advantages already described, several objects and advantages of the present invention are:
  (a) to provide a process which converts previously wasted energy in the form of the methane contained within ruminant animal exhalation to useful products;
  (b) to provide a process which provides a direct economic incentive for ruminant animal methane emission reductions;

(c) to provide a process which reduces ruminant animal methane emissions without altering the chemical or microbial make-up of the digestive tract of ruminant animals;

(d) to provide a process which reduces ruminant animal methane emissions without requiring ruminant animals to alter their normal/natural behavior patterns, including sleeping and nutrient-consumption;

(e) to provide a process which reduces ruminant animal methane emissions without requiring feed reformulations, selective breeding activities, or chemical or microbial modifications to the digestive systems of ruminant animals;

(f) to provide a process which can be integrated into ruminant animal ownership operations; and (g) to provide a process which converts an environmentally-destructive greenhouse gas into a beneficial, useful end-product.

Further objects and advantages will become apparent from a consideration of the drawings and ensuing description.

SUMMARY

In accordance with the invention a process wherein the methane contained within ruminant animal exhalation is utilized as a novel source of carbon and/or energy for the production of methane-utilizing microorganisms maintained in a microorganism growth-and-harvest system. This process may be accomplished by conveying the methane contained within ruminant animal exhalation to a microorganism growth-and-harvest apparatus wherein methane-utilizing microorganisms, a microorganism growth-culture medium, and the methane contained within ruminant animal exhalation are mutually-exposed, causing methane-utilizing microorganisms to grow.

DRAWINGS—FIGURES

FIG. 1 is a side perspective view of an apparatus used to carry out a process in accordance with the invention. In the illustration, the apparatus is self-contained and maintained entirely on the body of a ruminant animal. FIGS. 2A, 2B, 3A, and 3B describe this apparatus in greater detail.

DRAWINGS—REFERENCE NUMERALS

Figure 1:
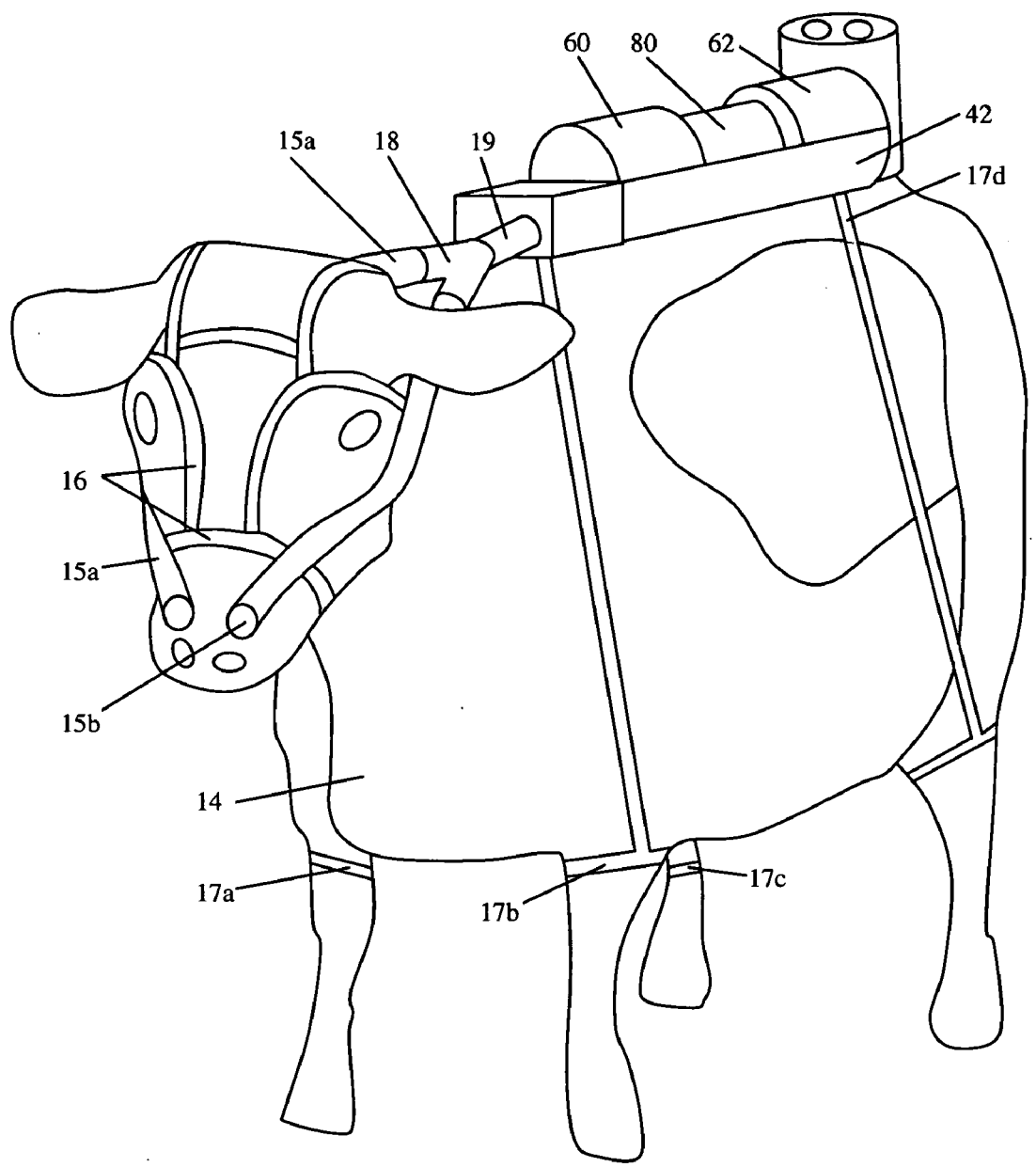

FIG. 1—Situation of Apparatus

Figure 2A:
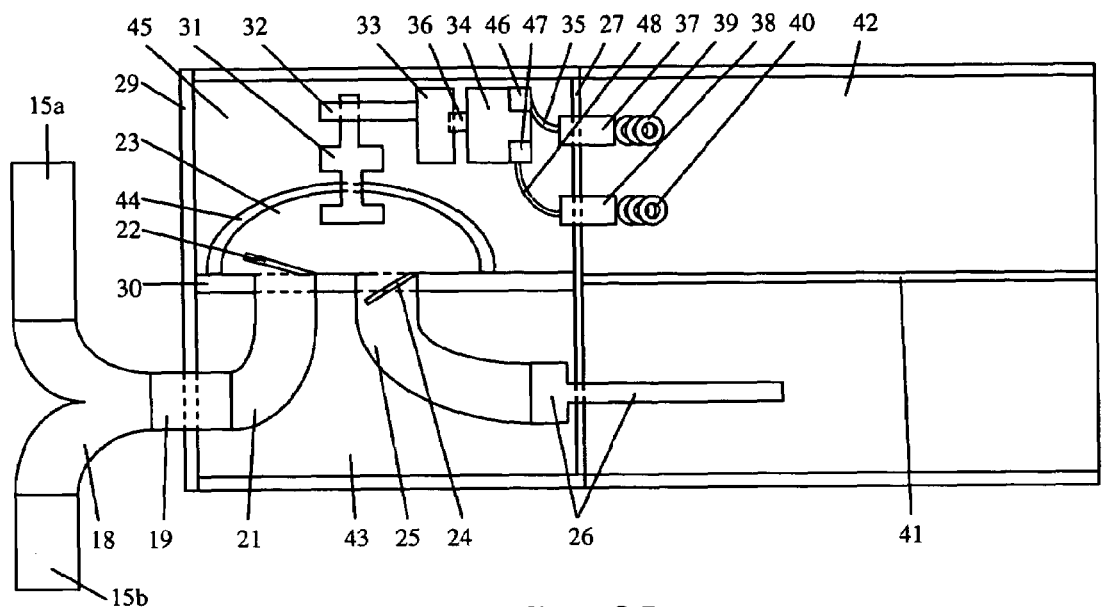
FIG. 2A is a Top cross-sectional view of one of two parts of the apparatus depicted in FIG. 1. The part of the apparatus illustrated is the permanent exhalation conveyance structure that is attached to the body of a ruminant animal.
Figure 2B:
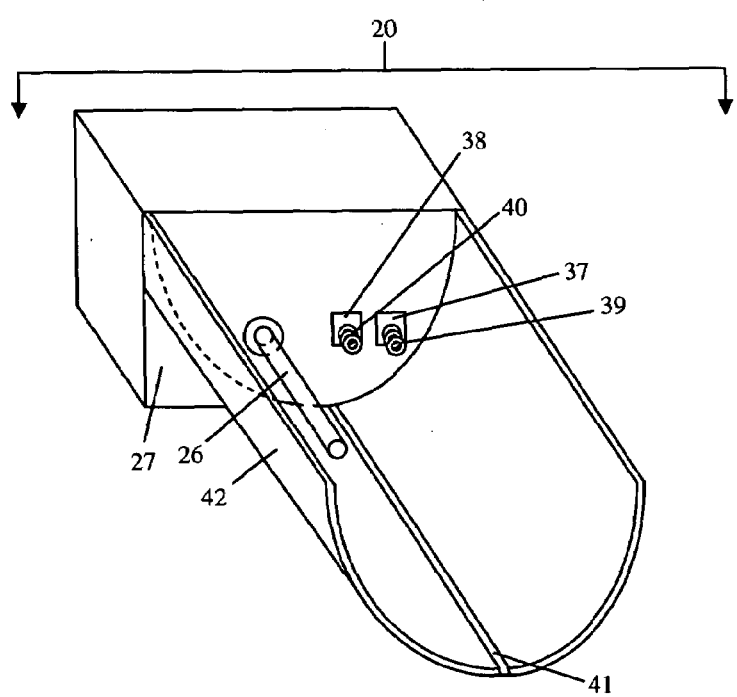
FIG. 2B is a Side perspective view of one of two parts of the apparatus depicted in FIG. 1. The part of the apparatus illustrated is the permanent exhalation conveyance structure that is attached to the body of a ruminant animal.
Figure 3A:
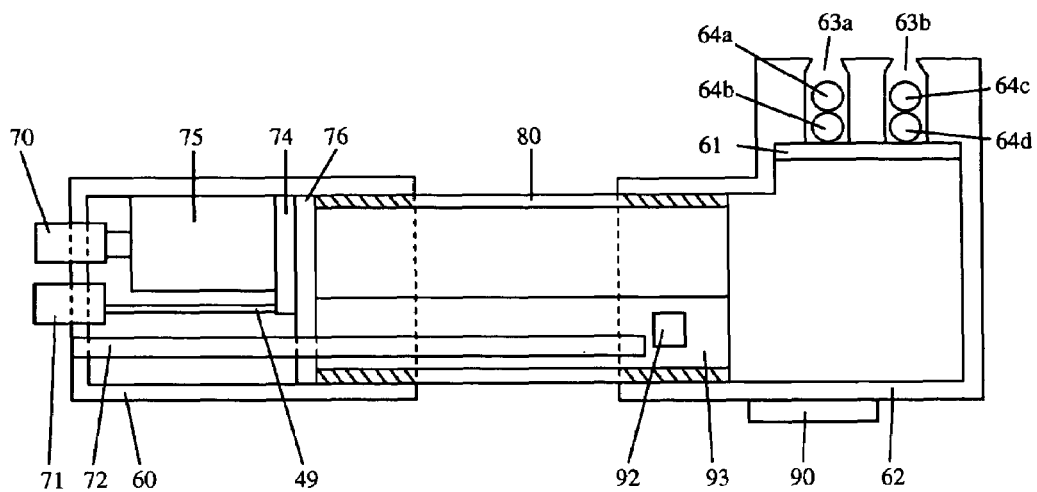
FIG. 3A is a Side cross-sectional view of one of two parts of the apparatus depicted in FIG. 1. The part of the apparatus illustrated is the removable microorganism containment capsule that is inserted into the permanent exhalation conveyance structure.
Figure 3B:
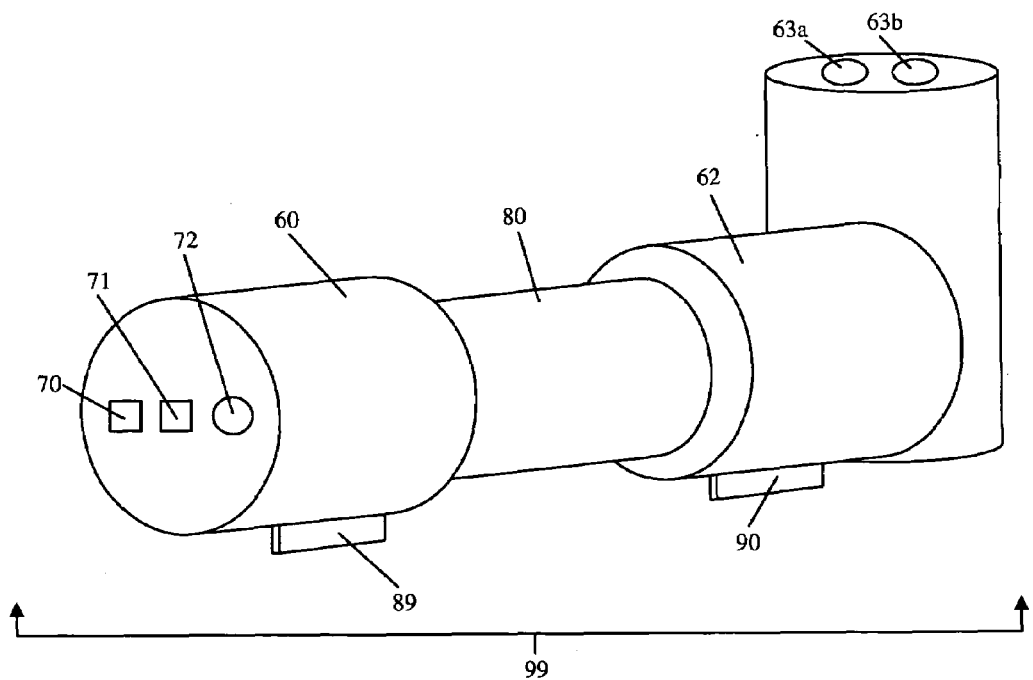
FIG. 3B is a Side perspective view of one of two parts of the apparatus depicted in FIG. 1. The part of the apparatus illustrated is the removable microorganism containment capsule that is inserted into the permanent exhalation conveyance structure.

14 Ruminant animal
15a Exhalation collection tube
15b Exhalation collection tube
Stationary head harness
17a Stabilizing leg strap
17b Stabilizing leg strap
Stabilizing leg strap
Stabilizing leg strap
Exhalation collection tube convergence T-pipe
Exhalation inflow tube FIGS. 2A and 2B—Permanent Exhalation Conveyance Structure
Permanent exhalation conveyance structure
Inflow pump chamber tube
Inflow one-way flap sphincter
Diaphragm-enclosed chamber
Outflow one-way flap sphincter
Outflow pump chamber tube
Outflow insertion needle
Air pump housing back wall
Air pump housing front wall
Air pump housing middle wall
Diaphragm pump plunger
Rotational gear tooth
Rotational gear
Direct-current rotational motor
Positive electrical conduction wire
Motor axle
Permanent structure positive conduction plate
Permanent structure negative conduction plate
Positive conduction continuation spring
Negative conduction continuation spring
Guidance groove
Half-cylindrical shell
Exhalation flow pipe chamber
Rubber diaphragm
Exhalation motor pumping chamber
Positive motor electrical terminal
Negative motor electrical terminal
Negative electrical conduction wire FIGS. 3A and 3B—Removable Microorganism Containment Capsule
Capsule negative electrical conduction wire
Threaded inflow attachment pipe
Wire mesh grating
Threaded outflow attachment pipe
Leak prevention hole
Leak prevention hole
Plug ball
Plug ball
Plug ball
Plug ball
Removable capsule positive electrical conduction terminal
Removable capsule negative electrical conduction terminal
Air dispersion capillary tube
Removable capsule negative electrical conduction plate
D-size battery
Inflow attachment pipe inner wall
Microorganism growth capsule pipe
Inflow guidance ridge
Outflow guidance ridge
Methane-utilizing microorganisms
Microorganism growth-culture medium
Removable microorganism containment capsule

DETAILED DESCRIPTION—PREFERRED

EMBODIMENT

While this invention is susceptible to embodiment in many different forms, there is shown in the drawings and will herein be described in detail a preferred method of carrying out a process in accordance with the invention with the understanding that the present disclosure is to be considered as an exemplification of the principles of the invention and is not intended to limit the broad aspect of the invention to the embodiment illustrated.

The subject invention pertains to the use of the methane contained within ruminant animal exhalation for the production of methane-utilizing microorganisms. More particularly, the present invention pertains to the use of the methane contained within ruminant animal exhalation (such methane henceforth referred to as "exhalation methane") for the production of methane-utilizing microorganisms in a microorganism growth-and-harvest apparatus. In the preferred embodiment, the method of the subject invention involves conveying exhalation methane to an apparatus situated entirely on the body of a ruminant animal which mutually-exposes methane-utilizing microorganisms, exhalation methane, and a microorganism growth-culture medium, causing methane-utilizing microorganisms to grow using exhalation methane as a source of carbon and/or energy.

FIG. 1 is a side perspective view of an apparatus used to carry out a process in accordance with the invention. In this illustration, all of the means necessary for carrying out a process in accordance with the invention are maintained and situated entirely on the body of ruminant animal, including means for conveying ruminant animal exhalation, and the exhalation methane therein, to a means for mutually-exposing exhalation methane, methane-utilizing microorganisms, and a microorganism growth-culture medium, as well as a means for harvesting the product of methane-utilizing microorganism growth.

In FIG. 1, exhalation collection tubes 15a and 15b are situated one on either side of the head of ruminant animal 14. Tubes 15a and 15b are held in place by stationary head harness 16 and lead up to the nostrils of ruminant animal 14. Tubes 15a and 15b run from the nostrils of ruminant animal 14 to where they both converge into exhalation collection tube convergence T-pipe 18. T-pipe 18 connects to exhalation inflow tube 19, which leads into permanent exhalation conveyance structure 20. Structure 20 is described in further detail by FIGS. 2A and 2B. Structure 20 is held in place on the back of ruminant animal 14 by stabilizing leg straps 17a, 17b, 17c, and 17d, as illustrated.

FIG. 2A is a top cross-sectional view of structure 20, and FIG. 2B is a side perspective view of structure 20. Tube 19 passes through air pump housing front wall 29 and leads into exhalation flow pipe chamber 43. Inside chamber 43, tube 19 connects to inflow pump chamber tube 21, which leads through chamber 43, through air pump housing middle wall 30, and into diaphragm-enclosed chamber 23. Where tube 21 opens into chamber 23 is inflow one-way flap sphincter 22, which, being a one-way flap, allows air to travel into chamber 23, but does not allow air to travel from chamber 23 into tube 21.

Chamber 23 is enclosed by rubber diaphragm 44. The open end of diaphragm 44 is attached to wall 30 so that an air-tight seal is made, and chamber 23 is formed. Diaphragm pump plunger 31 is inserted through and into diaphragm 44 on the side of diaphragm 44 farthest from wall 30. Plunger 31 extends out of diaphragm 44 to where it is joined perpendicularly to rotational gear tooth 32, which is attached to rotational gear 33. Gear 33 is mounted on motor axle 36, which leads into direct-current rotational motor 34. Motor 34 is located inside exhalation motor pumping chamber 45. Positive motor electrical terminal 46 is connected to permanent structure positive conduction plate 37 by positive electrical conduction wire 35. Negative motor electrical terminal 47 is connected to permanent structure negative conduction plate 38 by negative electrical conduction wire 48. Plate 37 and plate 38 are mounted on air pump housing back wall 27 with portions of each plate protruding through and outside of wall 27. Connected to the end of plate 37 on the end farthest from chamber 45 is positive conduction continuation spring 39. Connected to the end of permanent structure negative conduction plate 38 on the end farthest from chamber 45 is negative continuation spring 40. Structurally, an electric current can now flow from spring 39 to terminal 46 as well as from spring 40 to terminal 47.

Returning to chamber 23, outflow one-way flap sphincter 24 leads out from chamber 23 and into outflow pump chamber tube 25. Sphincter 24 allows air to travel out of chamber 23, but it does not allow air to travel from tube 25 into chamber 23. Tube 25 runs from chamber 23, through wall 30, and through chamber 43 to where it finally connects with outflow insertion needle 26. Needle 26 runs from the inside of chamber 43, protrudes through wall 27, and extends beyond wall 27 directly away from tube 19. Needle 26 is open on the end farthest from tube 25.

Half-cylindrical shell 42 is attached to wall 27. The orientation of shell 42 is depicted in FIG. 2B. Running the length of shell 42 is inlaid guidance groove 41. As will be described later, groove 41 has the purpose of guiding removable microorganism containment capsule 99 into correct orientation with needle 26, spring 39, and spring 40. Capsule 99 is described in greater detail in FIGS. 3A and 3B.

FIG. 3A and FIG. 3B depict capsule 99. Specifically, FIG. 3A is a side cross-sectional view of capsule 99, and FIG. 3B is a side perspective view of capsule 99. Structure 20 is designed to support and feed ruminant animal exhalation (and the methane contained therein) into capsule 99. Designed accordingly, capsule 99 is described in three parts: threaded inflow attachment pipe 60, threaded outflow attachment pipe 62, and microorganism growth capsule pipe 80. Capsule 99, as a whole, consists of each of these three pieces connected together, as will be described.

Pipe 80 is threaded on the outer side of both ends and contains methane-utilizing microorganisms 92 and microorganism growth-culture medium 93. In the present embodiment, 5 grams of Methylococcus capsulatus, methane-utilizing microorganisms which can be obtained from a number of biological supply depots (including Chang Bioscience, located at 125 Cambon Drive #6H, San Francisco, Calif. 94132) are placed in an aqueous microorganism growth-culture medium containing ammonium, nitrogen, and mineral salts.

Attached to one end of pipe 80 is pipe 60. Attached on the other end of pipe 80 is pipe 62. Pipe 60 houses D-size battery 75, which is situated between removable capsule positive electrical conduction terminal 70, removable capsule negative electrical conduction plate 74, and inflow attachment pipe inner wall 76. Plate 74 rests against wall 76 and sits adjacent to battery 75. Terminal 70 sits adjacent to battery 75 and protrudes through the front side of pipe 60. Similarly, terminal 71 protrudes through the front side of pipe 60 from the inside of pipe 60. Capsule negative electrical conduction wire 49 runs from terminal 71 to plate 74. Running from the outer edge of the front side of pipe 60, passing through wall 76, and extending beyond wall 76 into pipe 80 is air dispersion capillary tube 72. Tube 72 is a solid tube except for the portion extending into pipe 80, which contains tiny capillary holes in its walls that allow air to pass out of tube 72 but do not allow medium 93 to pass into tube 72. Tube 72 is open at the end meeting the outer edge of the front side of pipe 60, and closed at its opposite end. Attached to the outside of pipe 60 is inflow guidance ridge 89, a solid piece of material which will eventually fit into groove 41 illustrated in FIG. 2A and FIG. 2B.

Attached to pipe 80 on the end opposite pipe 60 is pipe 62. Pipe 62 is an elbow-shaped pipe that allows air to escape after it has passed through the small holes in the walls of tube 72. Pipe 62 is a hollow piece of piece of pipe at the end where it is connected to pipe 80, though, at its other end, pipe 62 is a solid piece of pipe. Wire mesh grating 61 is located inside pipe 62 at the border of where pipe 62 turns from hollow to solid. Still inside of pipe 62, adjacent to grating 61 in the solid portion of pipe 62, leak prevention holes 63*a* and 63*b* are drilled through the solid piece of pipe 62. Inside of hole 63*a* are plug balls 64*a* and 64*b*. Inside of hole 63*b* are plug balls 64*c* and 64*d*. Balls 64*a*, 64*b*, 64*c*, and 64*d* are rubber balls which can float on the surface of medium 93. Holes 63*a* and 63*b* are partially blocked at both the ends farthest and the ends closest to the hollow portion of pipe 62. Holes 63*a* and 63*b* are partially blocked by grating 61 at the end closest to the hollow portion of pipe 62. While the diameters of holes 63*a* and 63*b* are constant throughout, the diameters decrease at the ends farthest from the hollow portion of pipe 62 such that a single ball (64*a* or 64*c*) cannot pass through that end. Similar to ridge 89, outflow guidance ridge 90, which is able to slide into groove 41, is located on the outside of pipe 62.

Operation—FIGS. 1, 2A, 2B, 3A, and 3B

The following is a description of a method by which an apparatus is used to carry out a process in accordance with the invention.

First, structure 20 is situated on the back of ruminant animal 14 using straps 17*a*, 17*b*, 17*c*, and 17*d*. Next, harness 16 is attached to the head of ruminant animal 14, and tubes 15*a* and 15*b* are connected to harness 16 such that tubes 15*a* and 15*b* lead from T-pipe 18 up to the nostrils of ruminant animal 14.

Second, capsule 99 is placed into shell 42 of structure 20. This is accomplished by inserting ridge 89 and ridge 90 on capsule 99 into groove 41 inlaid in shell 42 of structure 20. With capsule 99 aligned with structure 20, capsule 99 is slid towards wall 27 up to the point where needle 26 is inserted into tube 72, and spring 39 and spring 40 are placed, respectively, into contact with terminal 70 and terminal 71. With terminal 70 and terminal 71 placed into contact with spring 39 and spring 40, respectively, an electrical current now runs from battery 75 in capsule 99 to motor 34 in structure 20. Specifically, a positive electrical current runs from battery 75, through terminal 70, through spring 39, through plate 37, though wire 35, to terminal 46. A negative electrical current runs from battery 75, through plate 74, through wire 49, through terminal 71, through spring 40, through plate 38, through wire 48, to terminal 47.

With an electrical current running from battery 75 to motor 34, axle 36 on motor 34 begins to rotate rapidly. As axle 36 rotates, gear 33 and gear tooth 32 also rotate rapidly, which in turn causes plunger 31 to rapidly push and pull diaphragm 44. With diaphragm 44 oscillating towards and away from wall 30, the motion of diaphragm 44 causes air to flow from tubes 15*a* and 15*b*, into chamber 23, and into needle 26. To expand, air is pulled through tubes 15*a* and 15*b*, through T-pipe 18, through tube 19, through tube 21, past sphincter 22, through chamber 23, past sphincter 24, through tube 25, and into needle 26.

With capsule 99 inserted, as described above, into structure 20, air now travels from needle 26 into tube 72. Since tube 72 is blocked at the end located in pipe 80 and since air cannot travel from tube 72 back into chamber 23, air is forced out through the tiny holes which exist in the walls of tube 72. To reiterate a detail mentioned above, tiny holes exist in the walls of tube 72 only where tube 72 extends into pipe 80. The result is that air is conveyed from needle 26, through tube 72, and into pipe 80. Eventually, with no other means of escape, the air inside pipe 80 flows into the hollow portion of pipe 62, past grating 61, into holes 63*a* and 63*b*, past plug balls 64*a*, 64*b*, 64*c*, and 64*d*, out of holes 63*a* and 63*b*.

The result of this conveyance of air is that as ruminant animal 14 exhales, this exhalation, as well as exhalation methane therein, is conveyed and directed into tubes 15*a* and 15*b*, which are situated just above the nostrils of ruminant animal 14. Exhalation methane now travels through tubes 15*a* and 15*b* to needle 26. With capsule 99 inserted, as described above, into structure 20, exhalation methane of ruminant animal 14 travels through needle 26 into pipe 80.

Pipe 80 contains microorganisms 92 and medium 93, and when exhalation methane is conveyed into pipe 80, microorganisms 92 grow and reproduce using this exhalation methane as a source of carbon and/or energy. Put differently, exhalation methane, microorganisms 92, and medium 93 are mutually-exposed in pipe 80. Thus, as more exhalation methane from ruminant animal 14 is exposed to microorganisms 92 in medium 93, microorganisms 92 grow and reproduce using exhalation methane as a source of carbon and/or energy. All excess gases, including waste carbon dioxide and waste exhalation methane, exit capsule 99 as described above.

Although medium 93 is an aqueous medium, holes 63*a* and 63*b*, balls 64*a*, 64*b*, 64*c*, and 64*d*, and grating 61 act together to prevent medium 93 from spilling or escaping out of capsule 99. Specifically, since plug balls 64*a*, 64*b*, 64*c*, and 64*d* are designed to float on the surface of medium 93, if medium 93 travels past grating 61 and moves into holes 63*a* and/or 63*b*, balls 64*a* and 64*c* will plug the small-diameter end of holes 63*a* and 63*b*, respectively, before the aqueous medium 93 can pass out of capsule 99.

The process continues when, after a certain amount of time (in this embodiment approximately 7 days) it is determined that microorganisms 92 within capsule 99 are no longer growing at optimal rates or have stopped growing completely, and capsule 99 is removed from structure 20. The microorganism growth process is re-started and continued simply by replacing previously-used capsule 99 with a new apparatus structurally identical to capsule 99 containing new methane-utilizing microorganisms and a new microorganism growth-culture medium. The process may also be continued by re-using capsule 99 and, after removing all or most of microorganisms 92 and medium 93, filling it with new microorganism growth-culture medium and an optimal number of new or previously used methane-utilizing microorganisms. In such a manner, exhalation methane is continually used as a source of carbon and/or energy for the growth and harvesting of methane-utilizing microorganisms.

Finally, microorganisms 92, having been grown in capsule 99 using exhalation methane as a source of carbon and/or energy, are removed from capsule 99 and harvested as useful biomass. (Methylococcus capsulatus has a biomass which consists of about seventy percent protein by weight.)

Such biomass can be processed and sold as a nutritional foodstuff or converted into other useful products, such as adhesives or cosmetics.

ADDITIONAL EMBODIMENTS

The present invention pertains to the use of exhalation methane as a novel source of energy for the production of methane-utilizing microorganisms in a confined growth-and-harvest apparatus existing outside of the digestive tract of a ruminant animal. There are a number of potential methods that can be used to carry out a process in accordance with the invention. In particular, there are a number of methods that can be utilized to mutually-expose exhalation methane, methane-utilizing microorganisms, and a microorganism growth-culture medium for the purpose of causing methane-utilizing microorganisms to grow using exhalation methane as a source of carbon and/or energy.

Such methods might include confining a ruminant animal to a site provided with means to funnel, convey, and/or direct exhalation methane into an apparatus whereby such exhalation methane is used to grow methane-utilizing microorganisms in a confined apparatus, and whereby the means used to carry out this process are either partially situated on a ruminant animal or not at all situated on a ruminant animal.

Such methods might also include providing means to convey exhalation methane from a site where ruminant animals are known to exhale frequently, such as feeding or sleeping areas, to a means for the mutual-exposure of exhalation methane, methane-utilizing microorganisms, and a microorganism growth-culture medium, whereby methane-utilizing microorganisms grow using exhalation methane as a source of carbon and/or energy in an apparatus existing outside of the digestive tract of a ruminant animal.

Such methods might also include causing methane-utilizing microorganisms to grow by mutually-exposing exhalation methane, methane-utilizing microorganisms, and a microorganism growth-culture medium in a confined apparatus, wherein some or all of the methane-utilizing microorganisms are genetically-engineered.

Such methods might also include growing methane-utilizing microorganisms using exhalation methane as a source of carbon and/or energy for such growth, whereby the means used to carry out the process are powered by solar, kinetic, methane-based, or other suitable form of power different from the source of power—battery power—mentioned in the above detailed description.

In any case, the detailed description of the preferred method of carrying out a process in accordance with the invention should serve foremost as an elucidation of the practical and technological feasibility of carrying out the invention, rather than as a limitation of the process of the invention itself.

CONCLUSION, SCOPE, RAMIFICATIONS

Accordingly, the reader will see that the invention, by providing a process for the novel utilization of the methane contained within the exhalation of a ruminant animal, provides a process which converts a previously wasted form of energy into a useful end-product, converts an environmentally-destructive gas into a useful end-product, provides a direct economic incentive for a ruminant animal methane emissions reduction effort, reduces ruminant animal methane emissions without altering the chemical or microbial make-up of the digestive tract of ruminant animals, reduces ruminant animal methane emissions without requiring ruminant animals to alter their normal/natural behavior patterns, including sleeping and nutrient-consumption, reduces ruminant animal methane emissions without requiring feed reformulations, selective breeding activities, or chemical or microbial modifications to the digestive systems of ruminant animals, can be integrated into ruminant animal ownership operations, utilizes as energy a material never previously considered a viable source of energy, and has the potential, if used widely, to significantly reduce ruminant animal methane emissions.

While the above description of a preferred method of carrying out a process in accordance with the invention contains many specificities, these should not be construed as limitations on the scope of the invention. As stated, there are a number of ways to carry out a process in accordance with invention. Accordingly, the scope of the invention should be determined not by the preferred method described, but by the appended claims and their legal equivalents.

I claim:

1. A method for producing methane-utilizing microorganisms in a confined apparatus comprising using the methane exhaled through ruminant animal exhalation as a source of carbon and/or energy for the growth of said microorganisms, comprising:

a. collecting methane gas that has been exhaled through ruminant animal exhalation, b. providing methane-utilizing microorganisms which can use said methane as a source of carbon and/or energy for growth, c. providing a growth-culture medium which promotes the growth of said microorganisms, including a nutrient substrate and/or a microorganism immobilization means, d. providing a means for the directed mutual-exposure of said methane, said microorganisms, and said growth-culture medium, including a means for the capture and conveyance of said methane and a means for confining said microorganisms, said growth-culture medium, and said methane to a specified apparatus existing outside of the digestive tract of a ruminant animal, e. mutually-exposing said methane, said microorganisms, and said growth-culture medium to cause said microorganisms to grow in said apparatus using said methane and said growth-culture medium, whereby said methane contained within said ruminant animal exhalation is utilized for the sustained growth of said microorganisms in a specified apparatus, whereby said methane, an environmentally-destructive material and previously unusable source of energy, is used to produce a useful end-product, and whereby said microorganisms can be harvested and utilized following growth, adding economic incentive to a ruminant animal methane emissions reduction effort.

2. The method of claim 1 wherein said conveyance means includes any means for conveying said methane within said ruminant animal exhalation to said mutual-exposure means.

3. The process of claim 2 wherein said conveyance means conveys said ruminant animal exhalation and said methane from the nostrils, mouth, or nostrils and mouth of a ruminant animal to said means of mutual-exposure.

4. The process of claim 1 wherein said mutual-exposure means comprises any means whereby said ruminant animal exhalation and said methane therein is conveyed and exposed to said methane-utilizing microorganisms and said growth-culture medium in said microorganism growth apparatus, whereby said methane-utilizing microorganisms reproduce in or on said growth-culture medium in said apparatus using said methane for growth.

5. The process of claim 4, including providing a means for causing said methane, said methane-utilizing microorganisms, and said growth-culture medium to be mutually-exposed in a batch, semi-batch, or continuous manner.

6. The process of claim 1 wherein said growth-culture medium comprises any medium promoting the growth of said microorganisms, including any liquid, semi-liquid, gas, particulate, ceramic, foam, plastic, alginate gel, clay, nutrient, or other appropriate growth-culture medium.

7. The process of claim 1 wherein said microorganisms are either naturally-occurring or genetically-engineered.

8. The method of claim 7 wherein said microorganisms either have or have not been previously exposed in said mutual-exposure means.

9. The method of claim 1, wherein the type of methane-utilizing microorganisms to be used in the confined apparatus is determined by one or more factors selected from the group consisting of the amount of growth desired, methane availability, and nutrient availability.

10. The process of claim 1, including providing a means to periodically harvest the product of said microorganism growth, including microorganism biomass and any other products associated with said growth.

11. The process of claim 1, including providing a means to periodically replace and/or renew said growth-culture means.

12. The process of claim 1, including providing a means to situate said means of mutual-exposure entirely on the body of a ruminant animal.

13. The process of claim 1, including providing a means to situate said means of conveyance, but not entire said mutual-exposure means, on a ruminant animal.

14. The process of claim 1 wherein no part of said means of mutual-exposure is situated on a ruminant animal.

* * * * *